United States Patent
Hindman et al.

(10) Patent No.: US 10,519,383 B2
(45) Date of Patent: Dec. 31, 2019

(54) INTEGRATED METHANOL SEPARATION AND METHANOL-TO-GASOLINE CONVERSION PROCESS

(71) Applicant: ExxonMobil Research and Engineering Company, Annandale, NJ (US)

(72) Inventors: Mitch L. Hindman, Spring, TX (US); Mohsen N. Harandi, New Hope, PA (US); Suriyanarayanan Rajagopalan, Spring, TX (US)

(73) Assignee: EXXONMOBIL RESEARCH AND ENGNEERING COMPANY, Annandale, NJ (US)

( * ) Notice: Subject to any disclaimer, the term of this patent is extended or adjusted under 35 U.S.C. 154(b) by 0 days.

(21) Appl. No.: 15/928,560

(22) Filed: Mar. 22, 2018

(65) Prior Publication Data
US 2018/0291280 A1    Oct. 11, 2018

Related U.S. Application Data

(60) Provisional application No. 62/481,862, filed on Apr. 5, 2017.

(51) Int. Cl.
*C10G 3/00* (2006.01)
*C07C 41/09* (2006.01)

(52) U.S. Cl.
CPC ............... *C10G 3/42* (2013.01); *C07C 41/09* (2013.01); *C10G 2300/202* (2013.01); *C10G 2400/02* (2013.01); *C10G 2400/20* (2013.01); *C10G 2400/22* (2013.01); *C10G 2400/30* (2013.01)

(58) Field of Classification Search
CPC .... C07C 1/20; C07C 1/26; C07C 1/22; C07C 1/24; C10G 3/49; C10G 2400/02; C10G 3/57; C10G 3/60; C10L 1/023; C10L 1/06
See application file for complete search history.

(56) References Cited

U.S. PATENT DOCUMENTS

| | | |
|---|---|---|
| 3,702,886 A | 11/1972 | Argauer et al. |
| 3,709,979 A | 1/1973 | Chu |
| 3,832,449 A | 8/1974 | Rosinski et al. |
| 3,931,349 A | 1/1976 | Kuo |
| 3,998,899 A | 12/1976 | Daviduk et al. |
| 4,016,218 A | 4/1977 | Haag et al. |
| 4,016,245 A | 4/1977 | Plank et al. |
| 4,035,430 A | 7/1977 | Dwyer et al. |
| 4,076,842 A | 2/1978 | Plank et al. |
| RE29,948 E | 3/1979 | Dwyler et al. |
| 4,234,231 A | 11/1980 | Yon |
| 4,417,000 A | 11/1983 | Slaugh et al. |
| 4,418,236 A | 11/1983 | Cornelius et al. |
| 4,556,477 A | 12/1985 | Dwyer |
| 4,709,113 A * | 11/1987 | Harandi .................. C07C 1/20 203/14 |
| 4,808,764 A | 2/1989 | Fremuth et al. |
| 2006/0135632 A1 | 6/2006 | Lattner et al. |

OTHER PUBLICATIONS

The International Search Report and Written Opinion of PCT/US2018/023759 dated May 22, 2018.

* cited by examiner

*Primary Examiner* — Sharon Pregler
(74) *Attorney, Agent, or Firm* — Liza Negron; Chad A. Guice

(57) ABSTRACT

A method for converting methanol to gasoline boiling range hydrocarbons is disclosed. In an aspect the method includes feeding crude methanol from a methanol synthesis reactor to a methanol separation vessel to recover a methanol stream in a vapor phase; and without condensing the methanol stream, feeding the methanol stream in the vapor phase to a reactor containing a conversion catalyst for converting methanol to at least one of dimethyl ether or gasoline boiling range hydrocarbons.

25 Claims, 1 Drawing Sheet

INTEGRATED METHANOL SEPARATION AND METHANOL-TO-GASOLINE CONVERSION PROCESS

CROSS-REFERENCE TO RELATED APPLICATIONS

Figure 1:
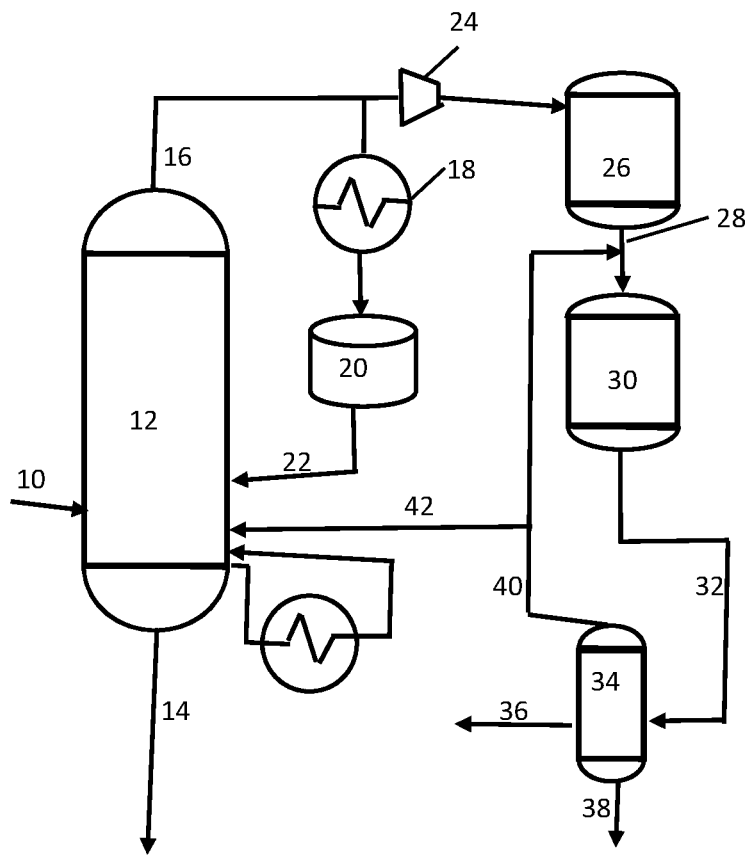

This application claims the benefit of U.S. Provisional Application No. 62/481,862 filed on Apr. 5, 2017, the entire contents of which are incorporated herein by reference.

FIELD

The present disclosure relates to systems and methods of producing gasoline boiling range hydrocarbons from methanol.

BACKGROUND

Processes for converting lower oxygenates such as methanol and dimethyl ether (DME) to hydrocarbons are known and have become of great interest because they offer an attractive way of producing liquid hydrocarbon fuels, especially gasoline, from sources which are not petrochemical feeds. In particular, they provide a way by which methanol and DME can be converted to gasoline boiling components, olefins and aromatics. Olefins and aromatics are valuable chemical products and can serve as feeds for the production of numerous important chemicals and polymers. Because of the limited supply of competitive petroleum feeds, the opportunities to produce low cost olefins from petroleum feeds are limited. However, methanol may be readily obtained from coal by gasification to synthesis gas and conversion of the synthesis gas to methanol by well-established industrial processes. As an alternative, the methanol may be obtained from natural gas or biomass by other conventional processes.

Available technology to convert methanol and other lower oxygenates to hydrocarbon products utilizes a fixed bed process, such as the processes described in U.S. Pat. Nos. 3,998,899; 3,931,349 and 4,035,430. In the fixed bed process, the methanol is usually first subjected to a dehydrating step, using a catalyst such as gamma-alumina, to form an equilibrium mixture of methanol, DME and water. This mixture is then passed at elevated temperature and pressure over a catalyst for conversion to the hydrocarbon products which are mainly in the range of light gas to gasoline. The fixed bed process uses a recycle gas for temperature control and very large heat transfer to manage low quality heat, which results in high compression costs and a large heat exchange network. Typically, a fixed bed process is a multi-reactor, unsteady state operation, which requires a large bore valving system to control the process.

In contrast, direct cooling of the reactor in the fluidized bed process eliminates the need for recycle gas for temperature control, which simplifies the heat exchange. Further, the fluidized bed process with continuous catalyst regeneration is a steady state operation with constant product yield. Thus, the fluidized bed process requires lower capital costs and savings on operating expenses compared to the fixed bed process. However, current fluidized bed processes typically require the methanol to be obtained from storage and the subjected to substantial preheating to vaporize and superheat the methanol before it is fed to the DME reactor.

SUMMARY

In one aspect, a method is provided for converting methanol to gasoline boiling range hydrocarbons. The method includes feeding crude methanol from a methanol synthesis reactor to a methanol separation vessel to recover a methanol stream in a vapor phase; and without condensing the methanol stream, feeding the methanol stream in the vapor phase to a reactor containing a conversion catalyst for converting methanol to at least one of dimethyl ether or gasoline boiling range hydrocarbons.

In another aspect, a method is provided for converting methanol to gasoline boiling range hydrocarbons comprising: feeding crude methanol from a methanol synthesis reactor to a methanol separation vessel to recover a methanol stream in a vapor phase; and feeding the methanol stream in the vapor phase to a reactor containing a conversion catalyst for converting methanol to at least one of dimethyl ether or gasoline boiling range hydrocarbons, wherein the separation vessel has a pressure that is substantially same as that of the reactor.

In yet another aspect, a method for converting methanol to gasoline boiling range hydrocarbons comprising: feeding crude methanol from a methanol synthesis reactor to a methanol separation vessel to recover a methanol stream in a vapor phase; and without condensing the methanol stream, compressing the methanol stream and feeding the methanol stream in the vapor phase to a reactor containing a conversion catalyst for converting methanol to at least one of dimethyl ether or gasoline boiling range hydrocarbons.

DRAWINGS

FIG. 1 is a schematic, illustrating a method of converting methanol to gasoline boiling range hydrocarbons according to one or more embodiments of the present invention.

DETAILED DESCRIPTION

Systems and methods are provided for converting methanol to gasoline boiling range hydrocarbons. Advantageously, such systems and methods may be employed at a methanol production plant. The systems and methods may include the feeding crude methanol from a methanol synthesis reactor to a methanol separation vessel to recover a methanol stream in a vapor phase. The methanol separation vessel may be, for example, a distillation unit or a separator drum. The methanol stream in the vapor phase may then be fed, without condensing the methanol stream to a reactor containing a conversion catalyst for converting methanol to at least one of dimethyl ether or gasoline boiling range hydrocarbons. This may be accomplished by operating the final methanol separation stage at approximately the same pressure as the reactor containing the conversion catalyst or by compressing the methanol stream to the pressure of the reactor.

As used herein, and unless specified otherwise, "gasoline" or "gasoline boiling range hydrocarbons" refers to a composition containing at least predominantly C5-C12 hydrocarbons. In one embodiment, gasoline or gasoline boiling range components is further defined to refer to a composition containing at least predominantly C5-C12 hydrocarbons and further having a boiling range of from about 100° F. to about 400° F. In an alternative embodiment, gasoline or gasoline boiling range components is defined to refer to a composition containing at least predominantly C5-C12 hydrocarbons, having a boiling range of from about 100° F. to about 400° F. at about 101.3 KPa absolute, and further defined to meet ASTM standard D439.

In some embodiments, the methods disclosed herein relate to methods in which a methanol separation vessel is operated at substantially the same pressure as a downstream reactor for converting the methanol to dimethyl ether or gasoline boiling range hydrocarbons or a combination thereof. As used herein "substantially the same pressure", when referring to the relative pressure of a first unit and a unit downstream of the first unit (such as a methanol separation vessel and a downstream reactor), means that the first unit has a pressure that is equal to the downstream unit plus the pressure needed to overcome the line losses between the units with an added margin of up to 5 psid. In other words, a methanol separation vessel is operating at substantially the same pressure as a downstream reactor when the pressure of the methanol separation unit is in the range of (a) to (b), wherein (a) is a lower bound defined by the pressure of the downstream reactor plus line losses, and (b) is an upper bound defined by the pressure of the downstream reactor plus line losses plus 5 psid. In embodiments, the term "substantially the same pressure" can includes a pressure difference of up to 20 psid, such as between 10 and 20 psid, such as between 10 and 15 psid.

An exemplary embodiment is illustrated in FIG. 1. A crude methanol feed 10, which may be obtained from a methanol synthesis unit, may be fed to a methanol separation unit 12 where water 14 and other impurities may be separated from the crude methanol feed 10. Methanol vapor 16 may be condensed to a liquid by condenser 18 to feed to a methanol storage tank 20 and/or fed in its vapor phase to a reaction unit where it is converted to gasoline boiling range hydrocarbons.

In some operating conditions, a methanol feed 22 may be taken from the storage tank 20 to either supplement the crude methanol feed 10 or to produce a methanol vapor stream 16 when the methanol synthesis unit is offline or otherwise not supplying crude methanol feed 10 to the methanol separation unit 12.

In any embodiment, an optional compressor 24 may be used to bring the methanol vapor stream 16 to the operating pressure of the first methanol conversion reactor. In an alternative embodiment, the separation unit 12 may be operated such that the last separation stage is substantially the same pressure as that of the first methanol conversion reactor.

In the illustrated embodiment, the first reactor is a DME reactor 26, which converts at least a portion of the methanol molecules to dimethyl ether, such as via a dehydration reaction. In such an embodiment, the DME reactor effluent 28 may contain an equilibrium mixture of methanol, dimethyl ether and water. The DME reactor effluent 28 may then be fed to one or more second reactors. The second reactor in the present illustration is an MTG reactor 30 which converts the DME reactor effluent 28 to gasoline boiling range hydrocarbons, which are provided as MTG product stream 32.

The MTG product stream 32 may then be fed to a product separation unit 34 for recovering the gasoline boiling range hydrocarbons 36. Water 38 may also be separated in this unit 34. Light gases and unconverted reactants 40 may be recirculated upstream of the MTG reactor 30 and/or may be used for a stripping gas in the separation unit 12 via stripping gas stream 42.

Methanol Synthesis

Methanol synthesis may be performed by any known process utilizing a methanol synthesis reactor. The methanol synthesis reactor may contain a catalyst for converting the synthesis gas to crude methanol. As used herein, the term "crude methanol" refers to the product of methanol synthesis that contains, in addition to methanol, water and unreacted components or impurities.

The catalysts for converting the syngas to methanol may be any of those known in the art which usually comprise copper, zinc oxide and alumina, zirconia and/or titania supports. Such catalysts are disclosed, for example, in U.S. Pat. No. 4,417,000. A particularly preferred catalyst comprises copper (measured as the metal) ranging from about 25% to about 65% by weight, basis total catalyst, more preferably ranging from about 35% to 55% by weight. The zinc oxide (as measured by the metal oxide) will range from about 35% by weight to about 65% by weight of the total catalyst, and preferably from about 40% by weight to 50%.

In any embodiment, the methanol synthesis may be performed utilizing gas-phase synthesis technology. In an exemplary embodiment, the reactor may be a loop reactor having a catalyst effective for converting a synthesis gas feed to a crude methanol product. The process may be performed at elevated pressures such as pressures exceeding 1000 psig, such as about 1400 psig, and at an inlet temperature of about 200 C to about 300 C.

The synthesis gas fed to the methanol synthesis reactor may be obtained from an integrated reformer, such as a steam reformer. In the reformer, a feedstock such as natural gas may be mixed with steam and converted to synthesis gas over a catalyst, such as a nickel catalyst, at elevated temperatures, such as temperatures greater than 800 C or about 880 C. The synthesis gas at the reformer outlet may be a mixture of hydrogen, carbon oxides and residual methane.

Methanol Separation

Crude methanol, received from a gas-phase synthesis reactor that uses synthesis gas with a stoichiometric number [molar ratio of (H2-CO2)/(CO+CO2)] of 2 or higher, may contain 25 to 35 mole % water. Methanol may be separated from the water as well as other lighter and heavier components using one or more separation vessels, such as distillation columns or separator drums.

The crude methanol may first be fed to a topping column where light ends, including unreacted methane, are separated from the methanol. Water and other heavy components may then be separated from the methanol in a refining column. Methanol is preferably recovered from the downstream separation vessel in the vapor phase.

Reboiler heat for the process may be obtained by cooling the syngas prior to it being fed to the methanol synthesis reactor. Although a two-column separation unit is described herein, one or more additional vessels may added to improve separation efficiency.

Methanol Conversion

Methanol may be converted to gasoline boiling range hydrocarbons in a methanol-to-gasoline ("MTG") process. Methanol, as recovered in the vapor phase, may then be fed to a methanol conversion reactor as a vapor phase feed. The methanol conversion reactor may contain a conversion catalyst for converting methanol to at least one of dimethyl ether ("DME") or gasoline boiling range hydrocarbons.

The vapor phase methanol from the separation vessel may be fed directly to the methanol conversion reactor either by compressing it to the operating pressure of the methanol conversion reactor or by increasing the pressure of the methanol separation vessel from which the vapor phase methanol is recovered to that of the methanol conversion reactor.

In an exemplary embodiment, the vapor phase methanol is fed to a first reaction stage in which methanol is converted via dehydration to an equilibrium mixture of methanol, dimethyl ether, and water. In a second stage, the equilibrium mixture may be passed over a catalyst to produce hydrocarbons and water. The second stage may be a series of reactions that result in formation of a hydrocarbon mixture that can comprise aromatics, paraffins, and olefins, among other types of hydrocarbon products.

C5+ gasoline yield in MTG processes can be in the range of 65-72 wt %, based on the feed, when relatively high temperatures (e.g., about 715-800° F.) and/or relatively low pressures (e.g., about 25-45 psig) are used in the MTG reactor. However, it is believed that the C5+ gasoline yield of the fluid bed MTG process can be improved to at least about 75 wt %, for example at least about 80 wt %, about 80-90 wt %, about 80-85 wt %, about 85-90 wt %, or about 86-95 wt %, as compared to the feed, advantageously without the need for an alkylation unit by staging the reactor, by operating the reactor at a higher pressure and lower temperature, and/or by recycling the light olefins. The spent catalysts from the reactor can be transferred to the regenerator to regenerate the catalyst by burning the coke off. The regenerated catalysts can then be transferred back to the reactor.

Alternatively or additionally, the oxygenate feedstock can comprise DME, which can be fed into a fluidized bed reactor and converted to gasoline boiling components. The DME to gasoline process can achieve a C5+ gasoline yield of greater than 70 wt %, for example at least about 75 wt %, at least about 80 wt %, about 75-95 wt %, about 75-90 wt %, about 80-90 wt %, about 80-85 wt %, about 85-90 wt %, or about 86-95 wt %, as compared to the feed, advantageously without the need for an alkylation unit by staging the reactor, by operating the reactor at a higher pressure and lower temperature, and/or by recycling the light olefins. The spent catalysts from the reactor can be transferred to the regenerator to regenerate the catalyst by burning the coke off. The regenerated catalysts can then be transferred back to the reactor.

In any embodiment, the fluidized bed reactor can include at least one layer of structured packing as a staging baffle. In various aspects, the fluid bed reactor can include from one to eight layers of structured packing. Advantageously, the fluid bed reactor can include at least two layers of structured packing.

The conversion reactions described herein typically utilize a catalyst. Useful catalyst compositions for MTG processes can comprise bound zeolite catalysts and unbound zeolite catalysts.

Generally, the zeolite employed in the present catalyst composition can typically have a silica to alumina molar ratio of at least 40, e.g., from about 40 to about 200. Additionally or alternatively, the zeolite can comprise at least one medium pore aluminosilicate zeolite having a Constraint Index of 1-12 (as defined in U.S. Pat. No. 4,016,218). Suitable zeolites can include, but are not necessarily limited to, ZSM-5, ZSM-11, ZSM-12, ZSM-22, ZSM-23, ZSM-35, ZSM-48, and the like, as well as combinations thereof. ZSM-5 is described in detail in U.S. Pat. No. 3,702,886 and RE 29,948. ZSM-11 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231. In certain embodiments, the zeolite can comprise, consist essentially of, or be ZSM-5. The ZSM-5 can have a silica to alumina ratio of 55:1.

When used in the present catalyst composition, the zeolite can advantageously be present at least partly in the hydrogen form. Depending on the conditions used to synthesize the zeolite, this may implicate converting the zeolite from, for example, the alkali (e.g., sodium) form. This can readily be achieved, e.g., by ion exchange to convert the zeolite to the ammonium form, followed by calcination in air or an inert atmosphere at a temperature from about 400° C. to about 700° C. to convert the ammonium form to the active hydrogen form. If an organic structure directing agent is used in the synthesis of the zeolite, additional calcination may be desirable to remove the organic structure directing agent.

The catalysts described herein can be pretreated with steam prior to use in the reactor.

To enhance the steam stability of the zeolite without excessive loss of its initial acid activity, the present catalyst composition can contain phosphorus in an amount between about 0.01 wt % and about 3 wt % elemental phosphorus, e.g., between about 0.05 wt % and about 2 wt %, of the total catalyst composition. The phosphorus can be added to the catalyst composition at any stage during synthesis of the zeolite and/or formulation of the zeolite and binder into the catalyst composition. Generally, phosphorus addition can be achieved by spraying and/or impregnating the final catalyst composition (and/or a precursor thereto) with a solution of a phosphorus compound. Suitable phosphorus compounds can include, but are not limited to, phosphinic [H2PO(OH)], phosphonic [HPO(OH)2], phosphinous, phosphorus, and phosphoric [PO(OH)3] acids, salts and esters of such acids, phosphorus halides, and the like, and combinations thereof. After phosphorus treatment, the catalyst can generally be calcined, e.g., in air at a temperature from about 400° C. to about 700° C. to convert the phosphorus to an oxide form.

In one embodiment, the catalyst is modified with up to 3 wt % phosphorous for improved stability.

Additionally or alternatively, the catalyst composition can include up to 80% clay by weight, for example up to 50 wt % clay, up to 40 wt % clay, or up to 30 wt % clay.

EMBODIMENTS

The following specific embodiments are also contemplated:

Embodiment 1

A method for converting methanol to gasoline boiling range hydrocarbons comprising: feeding crude methanol from a methanol synthesis reactor to a methanol separation vessel to recover a methanol stream in a vapor phase; and without condensing the methanol stream, feeding the methanol stream in the vapor phase to a reactor containing a conversion catalyst for converting methanol to at least one of dimethyl ether or gasoline boiling range hydrocarbons.

Embodiment 2

A method for converting methanol to gasoline boiling range hydrocarbons comprising: feeding crude methanol from a methanol synthesis reactor to a methanol separation vessel to recover a methanol stream in a vapor phase; and feeding the methanol stream in the vapor phase to a reactor containing a conversion catalyst for converting methanol to at least one of dimethyl ether or gasoline boiling range hydrocarbons, wherein the separation vessel has a pressure that is substantially same as that of the reactor.

Embodiment 3

A method for converting methanol to gasoline boiling range hydrocarbons comprising: feeding crude methanol from a methanol synthesis reactor to a methanol separation vessel to recover a methanol stream in a vapor phase; and without condensing the methanol stream, compressing the methanol stream and feeding the methanol stream in the vapor phase to a reactor containing a conversion catalyst for converting methanol to at least one of dimethyl ether or gasoline boiling range hydrocarbons.

Embodiment 4

Any of Embodiments 1 through 3, wherein the methanol separation vessel comprises a distillation unit or a separator drum.

Embodiment 5

Any of Embodiments 1 through 4, wherein the separation vessel has a pressure that is substantially same as that of the reactor.

Embodiment 6

The method of any of Embodiments 1 through 5, further comprising compressing the methanol stream in the vapor phase to a pressure that is substantially the same as that of the reactor.

Embodiment 7 the method of any of Embodiments 1 through 6, wherein the conversion catalyst is a dehydrogenation catalyst suitable for catalyzing the dehydrogenation of methanol to dimethyl ether and wherein the reactor operates under conditions suitable for converting the methanol stream into an intermediate product steam comprising dimethyl ether.

Embodiment 8 the method of any of Embodiments 1 through 7, further comprising feeding dimethyl ether in the intermediate product stream to a second reactor to convert the dimethyl ether to gasoline boiling range hydrocarbons.

Embodiment 9 the method of any of Embodiments 1 through 8, wherein the methanol is converted to a product comprising gasoline boiling range hydrocarbons and a lighter hydrocarbon fraction in the reactor or a separate downstream reactor; further comprising separating the lighter hydrocarbon fraction from the gasoline boiling range hydrocarbons.

Embodiment 10 the method of any of Embodiments 1 through 9, wherein at least a portion of the lighter hydrocarbon fraction is recycled to the reactor or the separate downstream reactor or a combination thereof.

Embodiment 11 the method of any of Embodiments 1 through 10, wherein at least a portion of the lighter hydrocarbon fraction is recycled to the methanol separation vessel.

Embodiment 12 the method of any of Embodiments 1 through 11, wherein the at least a portion of the lighter hydrocarbon fraction is used as a stripping stream in the methanol separation vessel.

Embodiment 13 the method of any of Embodiments 1 through 12, wherein the crude methanol comprises at least 15 mole % water.

The invention claimed is:

1. A method for converting methanol to gasoline boiling range hydrocarbons comprising:
feeding crude methanol from a methanol synthesis reactor to a methanol separation vessel to recover a methanol stream in a vapor phase; and
without condensing the methanol stream, feeding the methanol stream in the vapor phase to a reactor containing a conversion catalyst for converting methanol to at least one of dimethyl ether or gasoline boiling range hydrocarbons.

2. The method of claim 1, wherein the methanol separation vessel comprises a distillation unit or a separator drum.

3. The method of claim 1, wherein the separation vessel has a pressure that is substantially same as that of the reactor.

4. The method of claim 1, further comprising compressing the methanol stream in the vapor phase to a pressure that is substantially the same as that of the reactor.

5. The method of claim 1, wherein the conversion catalyst is a dehydration catalyst suitable for catalyzing the dehydration of methanol to dimethyl ether and wherein the reactor operates under conditions suitable for converting the methanol stream into an intermediate product steam comprising dimethyl ether.

6. The method of claim 5, further comprising feeding dimethyl ether in the intermediate product stream to a second reactor to convert the dimethyl ether to gasoline boiling range hydrocarbons.

7. The method of claim 1, wherein the methanol is converted to a product comprising gasoline boiling range hydrocarbons and a lighter hydrocarbon fraction in the reactor or a separate downstream reactor; further comprising separating the lighter hydrocarbon fraction from the gasoline boiling range hydrocarbons.

8. The method of claim 7, wherein at least a portion of the lighter hydrocarbon fraction is recycled to the reactor or the separate downstream reactor or a combination thereof.

9. The method of claim 7, wherein at least a portion of the lighter hydrocarbon fraction is recycled to the methanol separation vessel.

10. The method of claim 9, wherein the at least a portion of the lighter hydrocarbon fraction is used as a stripping stream in the methanol separation vessel.

11. The method of claim 1, wherein the crude methanol comprises at least 15 mole % water.

12. A method for converting methanol to gasoline boiling range hydrocarbons comprising:
feeding crude methanol from a methanol synthesis reactor to a methanol separation vessel to recover a methanol stream in a vapor phase; and
feeding the methanol stream in the vapor phase to a reactor containing a conversion catalyst for converting methanol to at least one of dimethyl ether or gasoline boiling range hydrocarbons, wherein the separation vessel has a pressure that is substantially same as that of the reactor.

13. The method of claim 12, wherein the methanol separation vessel comprises a distillation unit or a separator drum.

14. The method of claim 12, wherein the conversion catalyst is a dehydration catalyst suitable for catalyzing the dehydration of methanol to dimethyl ether and wherein the reactor operates under conditions suitable for converting the methanol stream into an intermediate product steam comprising dimethyl ether.

15. The method of claim 14, further comprising feeding dimethyl ether in the intermediate product stream to a second reactor to convert the dimethyl ether to gasoline boiling range hydrocarbons.

16. The method of claim 12, wherein the methanol is converted to a product comprising gasoline boiling range hydrocarbons and a lighter hydrocarbon fraction in the reactor or a separate downstream reactor; further comprising separating the lighter hydrocarbon fraction from the gasoline boiling range hydrocarbons.

17. The method of claim 16, wherein at least a portion of the lighter hydrocarbon fraction is recycled to the reactor or the separate downstream reactor or a combination thereof.

18. The method of claim 16, wherein at least a portion of the lighter hydrocarbon fraction is recycled to the methanol separation vessel.

19. A method for converting methanol to gasoline boiling range hydrocarbons comprising:

feeding crude methanol from a methanol synthesis reactor to a methanol separation vessel to recover a methanol stream in a vapor phase; and without condensing the methanol stream, compressing the methanol stream and feeding the methanol stream in the vapor phase to a reactor containing a conversion catalyst for converting methanol to at least one of dimethyl ether or gasoline boiling range hydrocarbons.

20. The method of claim 19, wherein the methanol separation vessel comprises a distillation unit or a separator drum.

21. The method of claim 19, wherein the conversion catalyst is a dehydration catalyst suitable for catalyzing the dehydration of methanol to dimethyl ether and wherein the reactor operates under conditions suitable for converting the methanol stream into an intermediate product steam comprising dimethyl ether.

22. The method of claim 21, further comprising feeding dimethyl ether in the intermediate product stream to a second reactor to convert the dimethyl ether to gasoline boiling range hydrocarbons.

23. The method of claim 19, wherein the methanol is converted to a product comprising gasoline boiling range hydrocarbons and a lighter hydrocarbon fraction in the reactor or a separate downstream reactor; further comprising separating the lighter hydrocarbon fraction from the gasoline boiling range hydrocarbons.

24. The method of claim 23, wherein at least a portion of the lighter hydrocarbon fraction is recycled to the reactor or the separate downstream reactor or a combination thereof.

25. The method of claim 23, wherein at least a portion of the lighter hydrocarbon fraction is recycled to the methanol separation vessel.

* * * * *